(12) United States Patent
Baruc

(10) Patent No.: US 10,548,692 B2
(45) Date of Patent: Feb. 4, 2020

(54) ANGULAR DENTAL ABUTMENT ASSEMBLY

(71) Applicant: T.A.G. Medical Devices—Agriculture Cooperative Ltd., Kibbutz Gaaton (IL)

(72) Inventor: Daniel Baruc, Nahariya (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 197 days.

(21) Appl. No.: 15/518,493

(22) PCT Filed: Oct. 12, 2015

(86) PCT No.: PCT/IL2015/051017
§ 371 (c)(1),
(2) Date: Apr. 12, 2017

(87) PCT Pub. No.: WO2016/059632
PCT Pub. Date: Apr. 21, 2016

(65) Prior Publication Data
US 2017/0231726 A1    Aug. 17, 2017

Related U.S. Application Data

(60) Provisional application No. 62/062,885, filed on Oct. 12, 2014.

(51) Int. Cl.
*A61C 8/00* (2006.01)
(52) U.S. Cl.
CPC ............ *A61C 8/0068* (2013.01); *A61C 8/006* (2013.01); *A61C 8/0056* (2013.01)
(58) Field of Classification Search
CPC ...... A61C 8/006; A61C 8/0056; A61C 8/0068
See application file for complete search history.

(56) References Cited

U.S. PATENT DOCUMENTS 4,932,868 A * 6/1990 Linkow ................ A61C 8/0018
433/174
5,002,489 A    3/1991 Fischer et al.
(Continued)

FOREIGN PATENT DOCUMENTS

CA        2853327      5/2013
CN      202069708     12/2011
(Continued)

OTHER PUBLICATIONS

International Search Report and the Written Opinion dated Jul. 1, 2016 From the International Searching Authority Re. Application No. PCT/IL2015/051017.

(Continued)

*Primary Examiner* — Cris L. Rodriguez
*Assistant Examiner* — Hao D Mai

(57) ABSTRACT

A dental abutment assembly that comprises a dental abutment having a tubular passage with an internal abutment thread at a lower end of the tubular passage, a dental implant fixture having an upper socket with an internal implant fixture thread, and a screw shaft having an upper external thread with an upper external helix twisted in a first direction and a lower external thread having a lower external helix twisted in a second direction, the upper external thread and the lower external thread are located at opposite ends of a connecting shaft. The first direction and the second direction are opposite to one another.

18 Claims, 6 Drawing Sheets

(56) References Cited

U.S. PATENT DOCUMENTS

| | | | |
|---|---|---|---|
| 5,094,618 A | | 3/1992 | Sullivan |
| 5,417,570 A | | 5/1995 | Zuest et al. |
| 5,695,336 A | | 12/1997 | Lazzara et al. |
| 6,012,923 A | | 1/2000 | Bassett et al. |
| 6,129,730 A | * | 10/2000 | Bono ................ A61B 17/8047 606/271 |
| 6,655,961 B2 | | 12/2003 | Cottrell |
| 8,628,327 B1 | | 1/2014 | Blaisdell et al. |
| 8,734,155 B2 | | 5/2014 | Bondar |
| 8,758,012 B2 | | 6/2014 | Hurson |
| 2003/0224328 A1 | * | 12/2003 | Sapian .................. A61C 8/005 433/173 |
| 2006/0172257 A1 | | 8/2006 | Niznick |
| 2008/0286720 A1 | | 11/2008 | Reed |
| 2009/0298013 A1 | * | 12/2009 | Baruc .................. A61C 8/005 433/174 |
| 2009/0318978 A1 | * | 12/2009 | Podgorski .......... A61B 17/7059 606/290 |
| 2010/0015571 A1 | | 1/2010 | Al-Attar et al. |
| 2010/0174324 A1 | * | 7/2010 | Derouet ............ A61B 17/8047 606/305 |
| 2010/0304329 A1 | * | 12/2010 | Heo .................... A61C 8/0089 433/146 |
| 2012/0172658 A1 | * | 7/2012 | Bjorn .................. H04R 25/606 600/25 |
| 2012/0178048 A1 | | 7/2012 | Cottrell |
| 2014/0147812 A1 | * | 5/2014 | Ilter .................... A61C 8/0001 433/174 |
| 2014/0162211 A1 | | 6/2014 | Mullaly et al. |
| 2014/0205969 A1 | * | 7/2014 | Marlin ................ A61C 8/0001 433/173 |
| 2015/0157426 A1 | * | 6/2015 | Choi ..................... A61C 8/006 433/174 |
| 2016/0278833 A1 | * | 9/2016 | Wong ................ A61B 17/8645 |

FOREIGN PATENT DOCUMENTS

| | | |
|---|---|---|
| DE | 10101907 | 7/2002 |
| EP | 2444024 | 4/2012 |
| EP | 2567672 | 3/2013 |
| WO | WO 98/52488 | 11/1998 |
| WO | WO 2006/065213 | 6/2006 |
| WO | WO 2012/170663 | 12/2012 |
| WO | WO 2013/014643 | 1/2013 |
| WO | WO 2013/059939 | 5/2013 |
| WO | WO 2014/093101 | 6/2014 |
| WO | WO 96/025895 | 6/2015 |
| WO | WO 2016/059632 | 4/2016 |

OTHER PUBLICATIONS

International Preliminary Report on Patentability dated Apr. 27, 2017 From the International Bureau of WIPO Re. Application No. PCT/IL2015/051017. (7 Pages).

Communication Pursuant to Article 94(3) EPC dated Oct. 9, 2018 From the European Patent Office Re. Application No. 15850906.7. (4 Pages).

Supplementary European Search Report and the European Search Opinion dated Apr. 11, 2018 From the European Patent Office Re. Application No. 15850906.7. (6 Pages).

* cited by examiner

ANGULAR DENTAL ABUTMENT ASSEMBLY

RELATED APPLICATIONS

This application is a National Phase of PCT Patent Application No. PCT/IL2015/051017 having International filing date of Oct. 12, 2015, which claims the benefit of priority under 35 USC § 119(e) of U.S. Provisional Patent Application No. 62/062,885 filed on Oct. 12, 2014. The contents of the above applications are all incorporated by reference as if fully set forth herein in their entirety.

FIELD OF THE INVENTION

The present invention relates to dental implants. More specifically, the present invention relates to an angular dental abutment assembly.

BACKGROUND

A dental implant fixture is used as a foundation for artificial teeth construction. It is a small post usually made of titanium that acts as a root structure for holding a prosthetic tooth.

It is known in the art to attach a dental prosthesis (crown, bridge of other dental appliances) to a patient's jaw using a dental implant fixture embedded in the patient's jaw. Between the dental implant fixture and the prosthesis a dental abutment is placed, serving as a mediator. One end of the dental abutment is fixed to the dental implant fixture, either internally or externally, while the other end is fixed to the prosthesis (normally inside the prosthetic tooth, in the form of a dental abutment). Collectively, the dental implant fixture, dental abutment, and the mechanism connecting the dental abutment to the assembly are called an implant assembly.

A dental implant fixture can be placed in the upper or the lower jaw bone, and after the bone has grown around the dental implant fixture, the dental implant fixture can hold a crown, a bridge or an over-denture just like roots hold natural teeth in place.

A key to dental implant fixture success is the quantity and quality of the bone where the dental implant fixture is to be positioned. In some patients, particularly in elderly people, the jaw bone may become thinner making it difficult to find a place for dental implants.

To overcome this difficulty, Paulo Malo from Nobel Biocare introduced the concept of "All-On-Four" which is a treatment solution based on four implants positioned on an elevated section of a retreating jawbone to obtain optimal positioning and support for a complete prosthetic denture. More specifically, the "All-On-Four" technique is based on tilting the two distal implants (typically of a total of four implants), which are implanted at the sides of the elevated section of the jawbone at an angle with respect to the jawbone and with respect to the remaining implants, so as to present an aligned and leveled foundation for a dental bridge or similar dental appliance.

SUMMARY

According to some embodiments of the present invention there is provided a dental abutment assembly, including a dental abutment having a tubular passage with an internal abutment thread at a lower end of the tubular passage, a dental implant fixture having an upper socket with an internal implant fixture thread, and a screw shaft having an upper external thread with an upper external helix twisted in a first direction and a lower external thread having a lower external helix twisted in a second direction where the upper external thread and the lower external thread are located at opposite ends of a connecting shaft where the first direction and the second direction are opposite to one another.

Optionally, the internal abutment thread is integrally formed within a polygonal end portion in the lower part of said dental abutment; where the polygonal end portion is a regular polygon.

Optionally, the upper socket is integrally formed with a polygonal hollow cavity that fittingly receives the polygonal end portion.

Optionally, the polygonal hollow cavity is cylindrical that fittingly receives an end portion of a lower part of the dental abutment.

Optionally, the polygonal hollow cavity is conical that fittingly receives an end portion of a lower part of the dental abutment.

Optionally, the tubular passage passes in a parallel projection of a longitudinal axis of the dental implant fixture.

Optionally, the abutment includes a prosthesis socket for receiving a prosthesis screw; where a longitudinal axis of the prosthesis socket and a longitudinal axis of the tubular passage are not parallel to one another.

Optionally, the upper portion of the dental abutment is integrally formed with a protruding ball.

Optionally, the upper portion of the dental abutment has a substantially planner surface.

Optionally, the diameter of the connecting shaft between the upper external thread and the lower external thread is smaller than a minor diameter of the internal abutment thread.

Optionally, the connecting shaft of the screw shaft between the upper external thread and the lower external thread has a smooth surface.

Optionally, the thread pitch of the upper external thread is different from the thread pitch of the lower external thread.

Optionally, the number of turns of a helix of the upper external thread is different from a number of turns of a helix of the lower external thread.

Optionally, the screw shaft has a screw head drive type selected from a group consisting of: a slot drive type and hex socket drive type.

According to some embodiments of the present invention there is provided a method of assembling a dental abutment assembly including implanting a dental implant fixture having an upper socket with an internal implant fixture thread in a jawbone of a human, providing a screw shaft having an upper external thread with an upper external helix twisted in a first direction and a lower external thread having a lower external helix twisted in a second direction where the upper external thread and the lower external thread are located at opposite ends of a connecting shaft; threading the upper external thread in an internal abutment thread located at a lower end of a tubular passage passing in a dental abutment, locating the dental abutment with the screw shaft above an upper part of the dental implant fixture, and applying a torque force on the screw shaft to thread the lower external thread into the internal implant fixture thread such that the torque force is converted to linear opposing forces pushing each of the dental implant fixture and the dental abutment towards the other of the dental implant fixture and the dental abutment.

Optionally, the threading of the upper external thread brings the internal abutment thread to cover a central portion of the screw shaft between the upper external thread and the lower external thread.

BRIEF DESCRIPTION OF THE SEVERAL VIEWS OF THE DRAWINGS

The present invention will be understood and appreciated more fully from the following detailed description, taken in conjunction with the drawings in which like components are denoted by like reference numerals.

DETAILED DESCRIPTION

According to an embodiment of the present invention, an angular abutment assembly is provided, comprising a dental implant fixture, a dental abutment, and a screw shaft. The screw shaft is a differential screw, with threading at both the upper and the lower ends of a shaft, wherein the direction of one threading is opposite handed from the direction of the other threading.

A dental prosthesis such as a crown, a bridge and/or any other dental prosthesis is to be fixedly fitted on the angular abutment. The dental abutment and screw shaft and dental implant fixture are fixedly connected in a manner that is described in detail herein below.

Figure 1:
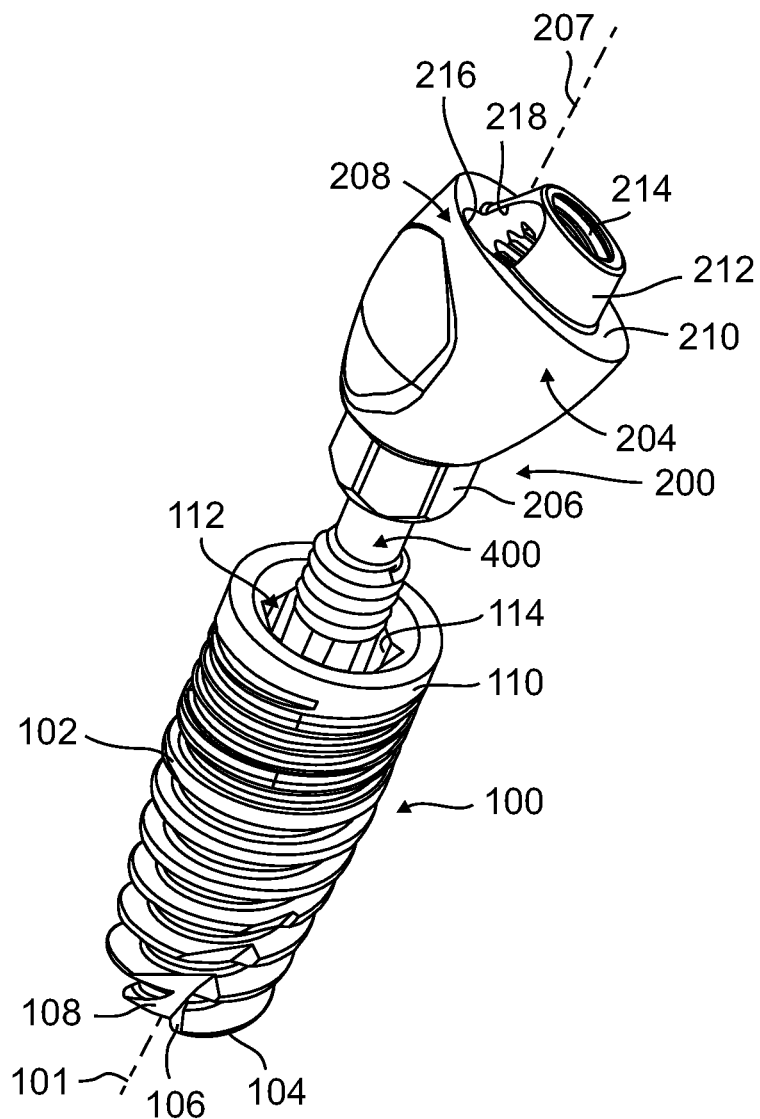
FIG. 1 illustrates a simplified isometric view of a dental implant fixture with a dental abutment assembly in accordance with an embodiment of the present invention.

Reference is now made to FIG. 1, which illustrates a simplified isometric view of a dental implant fixture 100 with a dental abutment assembly 200 comprising a dental abutment 204 and a screw shaft 400, wherein said dental implant and said screw shaft are securely fastened in a manner that will be described below, in accordance with an embodiment of the present invention.

Figure 2:
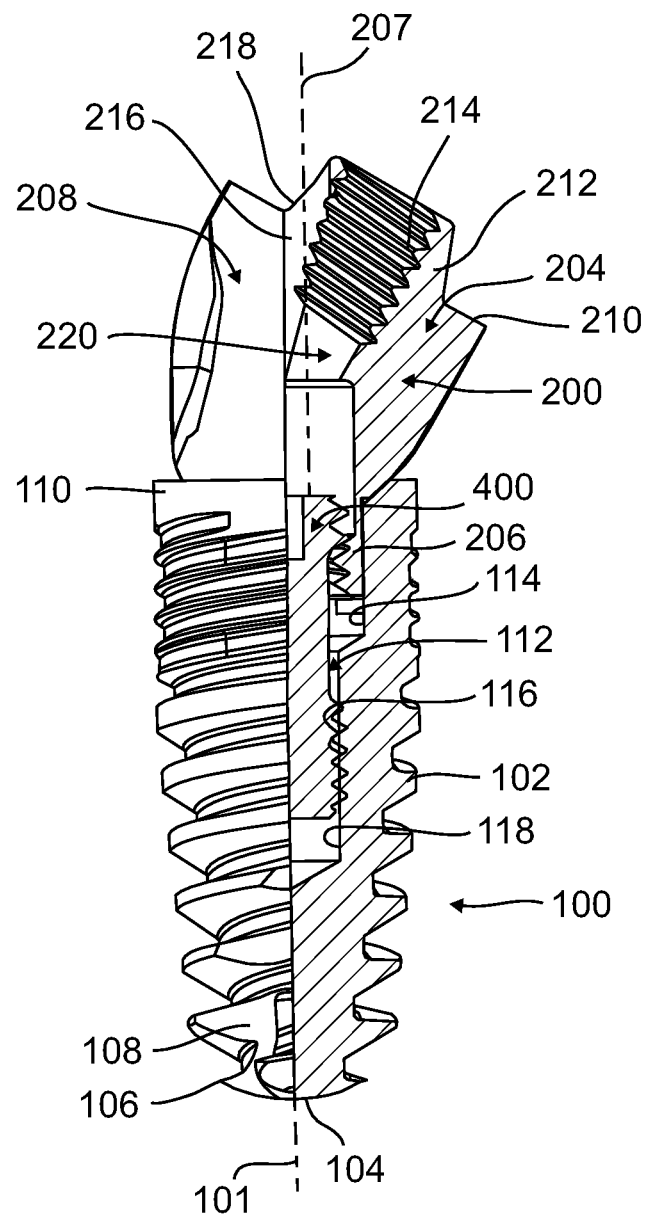
FIG. 2 illustrates a simplified longitudinal side-view and partial cross-section of the dental implant fixture with a dental abutment assembly shown in FIG. 1, in accordance with an embodiment of the present invention.

Reference is now made to FIG. 2, which illustrates a simplified longitudinal side-view and partial cross-section of the dental implant fixture 100 with a dental abutment 204 and the screw shaft 400 shown in FIG. 1.

A dental implant fixture 100 with a dental abutment 204 is seen in FIG. 1 and FIG. 2 in accordance with an embodiment of the present invention. The dental implant fixture 100 is arranged along longitudinal axis 101 and is provided with an outer threading 102 to allow the dental implant fixture to be screwed into a jawbone.

Figure 3A:
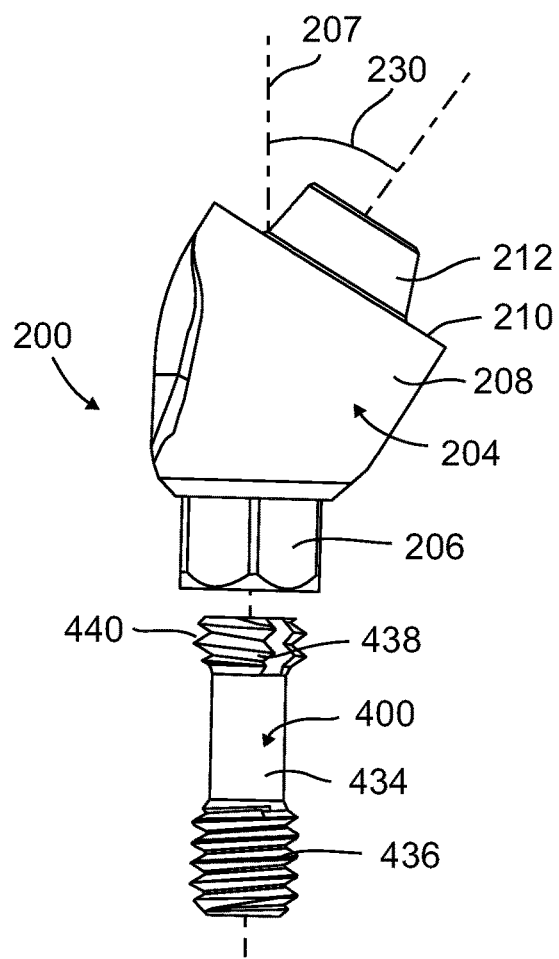
FIG. 3A is a simplified exploded view of parts of the dental abutment assembly shown in FIG. 1, in accordance with an embodiment of the present invention.
Figure 3B:
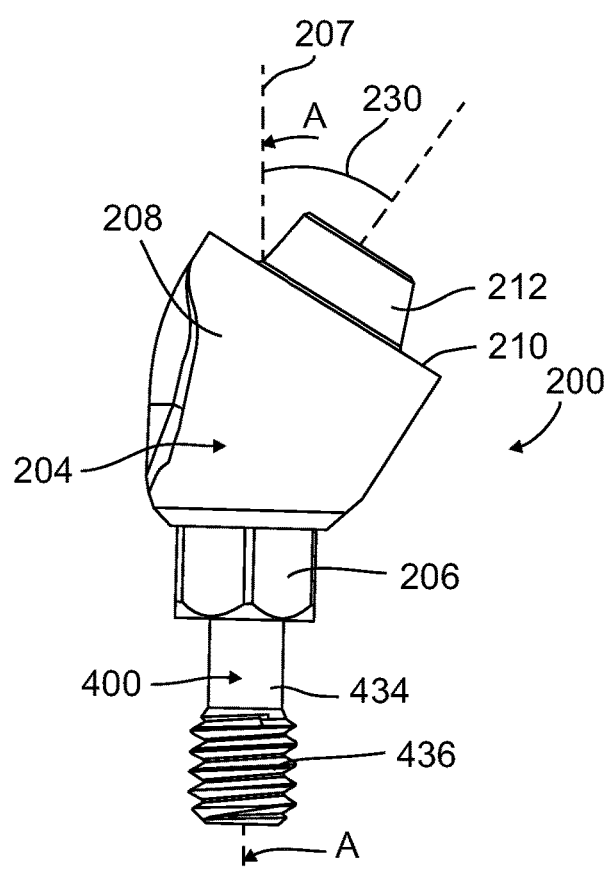
FIG. 3B is a simplified side-view illustration of the dental abutment assembly shown in FIG. 1, in an assembled state, in accordance with an embodiment of the present invention.

According to some embodiments of the present invention, as shown in FIG. 3B, the dental abutment assembly 200 can be provided in an assembled state, with the screw shaft and the dental abutment already interlocked, rendering the use of the dental abutment assembly by the dentist or technician more comfortable and simple. Providing the dental abutment assembly 200 in an assembled state also prevents the screw shaft from detaching from the dental abutment during attachment of the screw shaft to the dental implant fixture.

An advantage of the present invention, in some embodiments, is to control and limit the torque forces dental implant fixture 100 applies to the jawbone wherein the mechanical strength of the connection between the dental implant fixture and the dental abutment is not reduced. The reduction in torque forces on the jawbone is accomplished by means of the screw shaft, which has two threading, optionally with different thread pitch for each threading.

In existing art, dental abutments are attached to dental implant fixtures with a screw, such that when a torque force is applied to the screw, the screw compresses the dental abutment and the dental implant fixture towards each other. The force applied on the dental implant fixture and the dental abutment towards each other is herein referred to as vector A. When the dental abutment and dental implant fixture are fixedly in contact with each other the torque force applied to the screw is transferred to the dental implant fixture. The torque vector of the dental implant fixture is herein referred to as vector X. The magnitude of vector A and vector X are proportional to each other. Vector X is fixedly opposed by the tensile strength of the jawbone with a torque vector opposite in direction to vector X, herein referred to as vector Y. Vector Y prevents the dental implant fixture from rotating within the jawbone. Note that the tensile strength of the jawbone is an upper limit to the magnitude of vector X, thereby limiting the mechanical strength of the connection between the dental abutment and the prosthesis.

In the present invention, the screw shaft has two threadings, each with opposite handed threading. When a right handed torque is applied to the screw shaft, the dental implant fixture and the dental abutment are pulled towards each other. The force generated by the lower external thread is herein referred to as vector B, and the force generated by upper external thread is herein referred to as vector C. The sum of the magnitudes of vectors B and C are proportional to vector X. However, for a given vector X, the relative magnitudes of vectors B and vector C can be controlled by changing the thread pitch of the two threadings of the screw shaft.

A further advantage of the present invention is allowing the possibility to remove and/or exchange the screw shaft without damaging jawbone surrounding the dental implant fixture.

To attach screw shaft 400 and dental abutment 204, upper external thread 440 is threaded into internal abutment thread 232 until upper external thread 440 extends upwardly beyond internal abutment thread 232. Connecting shaft 434 of screw shaft 400 is now surrounded by internal abutment thread 232, and screw 202 is interlocked within dental abutment 204.

Lower end 104 of dental implant fixture 100 is provided with one or more cutting edges 106 and one or more flutes 108. Both the cutting edges 106 and the flutes 108 allow dental implant fixture 100 to function as a self-tapping screw that is screwed into the jawbone tissue, the flute designed to accommodate bone and tissue debris.

Upper end 110 of dental implant fixture 100 has a smooth outside peripheral surface designed to remain above the bone (yet embedded in the surrounding soft tissue) and includes an upper socket 112 of dental implant fixture 100 with polygonal hollow cavity 114. It is appreciated that alternatively the upper portion 114 can be formed as an octagon, pentagon, slotted socket, conical socket and/or any other suitable geometrical shape.

It is specifically seen in FIG. 2 that upper socket 112 of dental implant fixture 100 includes polygonal hollow cavity 114, threaded middle portion 116 and smoothly surfaced bottom portion 118. According to some embodiments of the present invention, threaded middle portion 116 has right handed threading. Threaded middle portion 116 is provided for enabling threaded attachment of screw 400 to dental implant 100.

It is a particular feature of some embodiments of the present invention that the dental abutment 204 is integrally formed with a polygonal end portion 206. The polygonal end portion 206 may be formed as an octagon, pentagon, slotted socket, conical socket and/or any other suitable geometrical shape. Hexagonal upper portion 114 receives the polygonal end portion 206 of dental abutment 204.

It is a particular feature of some embodiments of the present invention that polygonal end portion 206 is formed with an internal abutment thread 232, which in accordance with an embodiment of the present invention is left handed. Internal abutment thread 232 enables threaded attachment of screw 400 to the dental abutment 204.

Upper portion 208 of dental abutment 204 is provided with a protruding flange 212 with socket 214 and tubular passage 216, wherein socket 214 opens to internal threaded socket 215. Socket 214 and tubular passage 216 may be identified in FIG. 1.

Reference is now made to FIG. 3A which is a simplified exploded view of parts of the dental abutment assembly 200 shown in FIG. 1, in accordance with some embodiments of the present invention.

Figure 4:
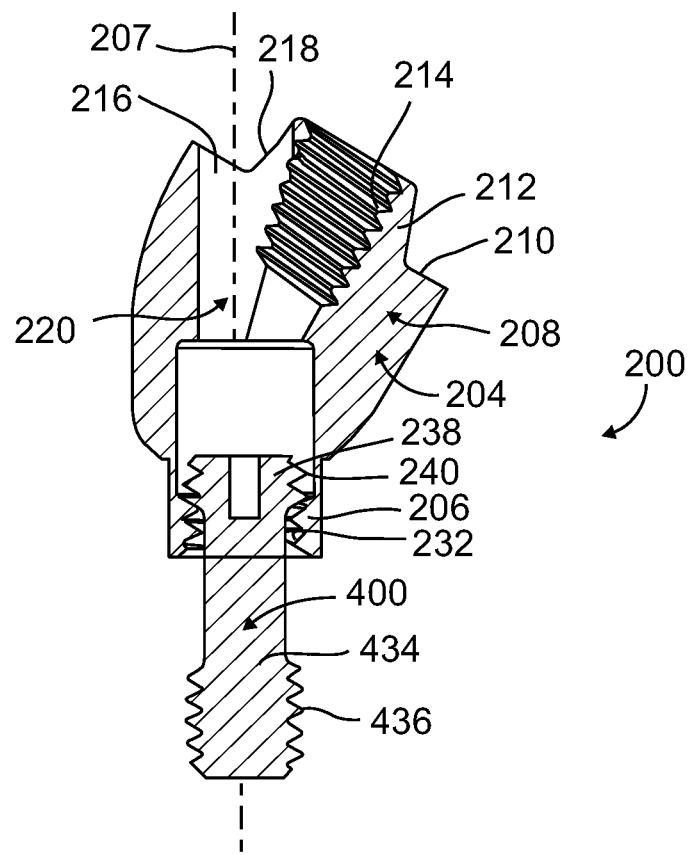
FIG. 4 is a simplified cross-sectional side-view illustration of the dental abutment assembly shown in FIG. 1, taken along section lines A-A in FIG. 3B, in accordance with an embodiment of the present invention.

Reference is now made to FIG. 3B, which is a simplified side-view illustration of the dental abutment assembly 200 shown in FIG. 1, in an assembled state and to FIG. 4, which is a simplified cross-sectional side-view illustration of the dental abutment assembly 200 shown in FIG. 1, taken along section lines A-A in FIG. 3B.

The plane of surface 210 of dental abutment 204 is inclined with respect to the longitudinal axis 207 of dental abutment 204. The angle 230 of dental abutment 204 delineates the angle formed by axis 207 and the perpendicular to the plane of surface 210. Angle 230 may vary and it is noted that for "all-on-four" technique purposes typical inclination angles include 15, 17, 30 degrees and the like.

As seen in FIG. 3A, screw shaft 400 includes a connecting shaft 434, screw slot 438, lower external thread 436 which in some embodiments of the present invention has right handed threads, and upper external thread 440 which in some embodiments of the present invention has left-handed thread. It is a particular feature of an embodiment of the current invention that the diameter of connecting shaft 434 is smaller than the minor diameter of internal abutment thread 232.

Optionally the thread pitch of the lower external thread 436 and the upper external thread 440 may differ from each other. For example, the upper external thread 440 may have a smaller pitch than lower external thread 436. In some embodiments of the present invention the length of connecting shaft 434, the length of lower external thread 436, and the length of polygonal hollow cavity 114 are such that when locating dental abutment 200 onto implant 100, polygonal end portion 206 is partially or fully seated within polygonal hollow cavity 114, thereby preventing rotation of dental abutment 200 relative to dental implant fixture 100 along the longitudinal axis.

Reference is now made to a process of assembling dental implant fixture 100, screw shaft 400, and dental abutment 204 according to some embodiments of the present invention. Prior to locating dental abutment 204 above dental implant fixture 100, the dental abutment assembly 204 is assembled by interlocking the dental abutment 200 and the screw shaft 400 in the manner described above. Abutment assembly 200 is then located above dental implant fixture 100 such that polygonal end portion 206 is within the polygonal hollow cavity 114 and lower external thread 436 is in contact with the internal threads of threaded middle portion 116.

Right-handed torque may be applied to screw shaft 400, such that the threads of lower external thread 436 engage with the threads of internal implant fixture thread 116, and the left-handed threads of upper external thread 440 prevent detachment of screw 202 from the dental abutment 204. Torque may be applied to screw shaft 204 by means of a dental torque wrench and/or screwdriver blade inserted in screw slot 438. Tubular passage 216 provides access to screw slot 438.

Reference is now made to FIG. 4. Torque is applied to the screw shaft 400. Said torque is converted to linear forces pushing each of said dental implant fixture and said dental abutment towards the other of said dental implant fixture and said dental abutment. After the fixed attachment of dental abutment 204 to dental implant fixture 100, axis 101 of the dental implant fixture and axis 207 of the dental abutment are aligned.

Optionally, the dental abutment assembly is not assembled prior to locating dental abutment 204 on the dental implant fixture 100. In this embodiment, referred to herein as manual assembly, lower external thread 436 of screw shaft 400 is inserted into upper socked 112 of dental implant 100 wherein lower external thread 436 contacts internal implant fixture thread 116. Next dental abutment 200 is located above screw 400 and dental implant 100 such that internal abutment thread 232 is in contact with upper external thread 440. Right-handed torque may be applied to screw shaft 400, such that the threads of lower external thread 436 engage with the threads of internal implant fixture thread 116, and the left-handed threads of upper external thread 440 engage with internal abutment thread 232. Said torque is converted to linear opposing forces pushing each of said dental implant fixture and said dental abutment towards the other of said dental implant fixture and said dental abutment.

As seen in FIG. 1 in some embodiments of the present invention the dental abutment 204 has socket 214 with internal threaded socket 215, allowing fixedly a dental prosthesis to the dental abutment assembly.

Figure 5:
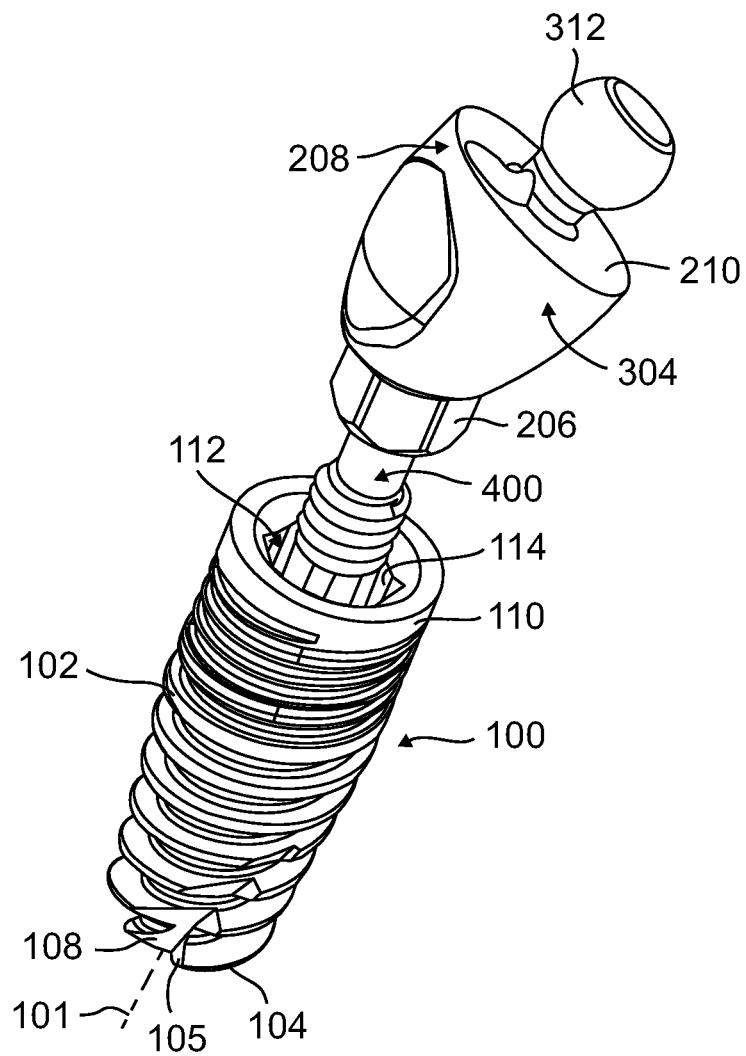
FIG. 5 illustrates a simplified isometric view of a dental implant fixture with a dental abutment assembly in accordance with another embodiment of the present invention.
Figure 6:
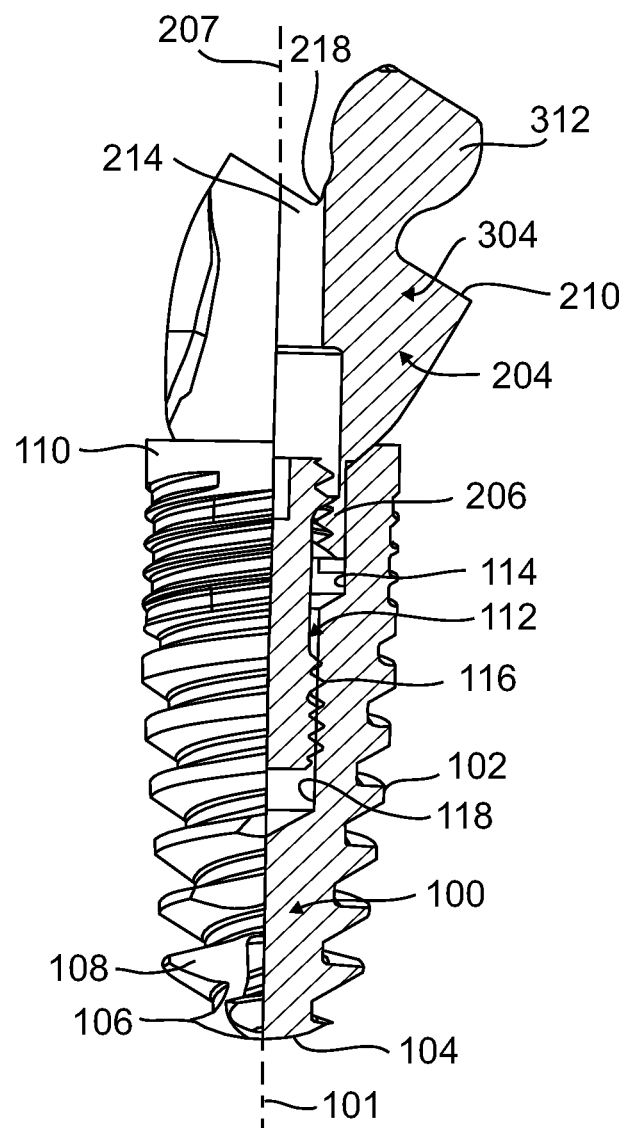
FIG. 6 illustrates a simplified longitudinal side-view and partial cross-section of the implant fixture with an abutment assembly shown in FIG. 5.

Reference is now made to FIG. 5, which illustrates a simplified isomeric view of a dental implant fixture with a dental abutment assembly in accordance with an embodiment of the present invention. As shown in FIG. 5, optionally dental abutment 204 may be configured with a protruding ball attachment 312. Protruding ball 312 allows attachment of a prosthesis with a complimentary ball socket to dental abutment 204. Abutment 304 has protruding ball 312, which differs from dental abutment 204 which has protruding flange 212 and socket 214. In all other aspects, dental abutments 204 and 304 are identical.

According to some embodiments of the present invention the hexagonal shape of polygonal end portion 206 of dental abutment 204 and the corresponding hexagonal shape of polygonal hollow cavity 114 of the dental implant fixture 100 allow aligning the dental abutment 204 in six different and distinct orientations with respect to the dental implant fixture 100.

Optionally, polygonal end portion 206 and polygonal cavity 114 may both be any regular polygon wherein having the same number of sides and wherein end portion 114 receives polygonal end portion 206. The number of distinct alignments along longitudinal axis 101 of dental abutment 204 relative to dental implant fixture 100 corresponds to the number of sides of the regular polygons.

Optionally, when some rotational freedom is desired or more specifically, when the desired structure should include a dental abutment coaxially rotatable about the longitudinal axis of dental implant fixture 100, the polygonal end portion 206 should be replaced by an internally threaded retainer with a circular body.

Optionally all right handed threading and left handed threading and right handed torque may be changed to opposite handed threading and opposite handed torque.

Optionally, the drive type of slot 438 of screw 400 may be selected from a group consisting of: hex socket drive type and slot drive type.

The dental abutment described in the present specification and accompanying figures is either snapped and/or screwed into the adjacent prosthesis, but it is noted that other attachment techniques, for example cementing, with which the dental abutment is attached to the prosthesis are also covered by the scope of the present invention.

The dental implant fixture may be made from a variety of materials, comprising biocompatible Titanium alloy and/or other materials. Generally, the length of the dental implant fixture may be 4 millimeters or as long as 20 millimeters. Generally, the diameter of dental implant fixture may be 2 millimeters or as wide as 8 millimeters.

The screw shaft may be made from a variety of materials, comprising commercially pure titanium, coated titanium, treated titanium, gold, and/or any other materials. Generally the length of the screw shaft is 4 millimeters or as long as 20 millimeters. Generally the diameter of the screw shaft may be 1.5 millimeters or as wide as 8 millimeters.

Lower screw thread 436 and upper external thread 440 screw shaft 400 may have as few as 2 helix threads and as many as 25 helix threads.

While some embodiments of the present invention were described with reference to the "all-in-four" technique, it is understood that it may be also used for other dental restoration appliances and techniques, and the scope of the present invention is not limited to the "all-in-four" technique.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

What is claimed is:

1. A dental implant assembly having a proximal end and a distal end, said distal end configured to be screwed into a jawbone, said dental implant assembly comprising:
   a dental abutment configured to be positioned at said proximal end of said assembly, said dental abutment having a tubular passage with an internal abutment thread at a distal end of said tubular passage;
   a dental implant fixture having a proximal socket with an internal implant fixture thread, wherein a distal end of said dental abutment is receivable in said proximal socket; and
   a screw shaft having a proximal external thread, a distal external thread and a connecting shaft, said proximal thread and distal thread located at opposite ends of said connecting shaft;
   wherein said connecting shaft comprises a smooth surface and a diameter smaller than a minor diameter of said internal abutment thread;
   wherein said proximal external thread is sized and shaped for being threaded into said internal abutment thread; and
   when said assembly is assembled:
      a) said entire proximal external thread extends proximally beyond said internal abutment thread; and
      b) said connecting shaft is surrounded by said internal abutment thread.

2. The dental implant assembly according to claim 1, wherein said internal abutment thread is integrally formed within a polygonal end portion in a distal part of said dental abutment; wherein said polygonal end portion is a regular polygon.

3. The dental implant assembly according to claim 2, wherein said proximal socket is integrally formed with a polygonal hollow cavity that fittingly receives said polygonal end portion.

4. The dental implant assembly according to claim 3, wherein said polygonal hollow cavity is cylindrical that fittingly receives an end portion of said distal part of said dental abutment.

5. The dental implant assembly according to claim 3, wherein said polygonal hollow cavity is conical that fittingly receives an end portion of said distal part of said dental abutment.

6. The dental implant assembly according to claim 1, wherein said tubular passage passes in a parallel projection of a longitudinal axis of said dental implant fixture.

7. The dental implant assembly according to claim 1, said dental abutment further comprising a prosthesis socket for receiving a prosthesis screw; wherein a longitudinal axis of said prosthesis socket and a longitudinal axis of said tubular passage are not parallel to one another.

8. The dental implant assembly according to claim 1, wherein a proximal portion of said dental abutment is integrally formed with a protruding ball.

9. The dental implant assembly according to claim 1, a proximal portion of said dental abutment having a substantially planar surface.

10. The dental implant assembly according to claim 1, wherein a thread pitch of said proximal external thread is different from a thread pitch of said distal external thread.

11. The dental implant assembly according to claim 1, wherein a number of turns of a helix of said proximal external thread is different from a number of turns of a helix of said distal external thread.

12. The dental implant assembly according to claim 1, said screw shaft having a screw head drive type selected from a group consisting of: a slot drive type and a hex socket drive type.

13. The dental implant assembly of claim 1, wherein said abutment tubular passage comprises a wide portion proximal to said internal abutment thread having a diameter larger than a major diameter of said proximal external thread.

14. The dental implant assembly of claim 13, wherein said abutment tubular passage comprises a narrow portion to provide access of a tool to a screw slot on said screw shaft.

15. The dental implant assembly of claim 1, wherein said distal external thread and proximal external thread comprise between 2 and 25 helix threads.

16. The dental implant assembly of claim 1, wherein a helix of said proximal external thread is twisted in a first direction and a helix of said distal external thread is twisted in a second direction.

17. A method of assembling a dental implant assembly having a proximal end and a distal end, said distal end configured to be screwed into a jawbone, said method comprising:

providing a dental abutment configured to be positioned at said proximal end of said assembly, said dental abutment having tubular passage with an internal abutment thread located at a distal end of the tubular passage;

providing a screw shaft having a proximal external thread and a distal external thread located at opposite ends of a connecting shaft having a smooth surface;

threading said proximal external thread in the internal abutment thread until said proximal external thread entirely passes said internal abutment thread;

providing a dental implant fixture having a proximal socket with an internal implant fixture thread; and screwing a distal end of said dental abutment into the dental implant fixture proximal socket.

18. The method according to claim 17, wherein said threading of said proximal external thread brings said internal abutment thread to surround said smooth surfaced connecting shaft.

\* \* \* \* \*